United States Patent [19]

Rozzell

[11] Patent Number: 4,525,454
[45] Date of Patent: Jun. 25, 1985

[54] PRODUCTION OF L-4-PHENYL-2-AMINOBUTANOIC ACID BY TRANSAMINATION

[75] Inventor: J. David Rozzell, Cambridge, Mass.

[73] Assignee: Genetics Institute, Inc., Boston, Mass.

[21] Appl. No.: 643,654

[22] Filed: Aug. 23, 1984

Related U.S. Application Data

[63] Continuation-in-part of Ser. No. 528,730, Sep. 4, 1983.

[51] Int. Cl.$^3$ .................. C12P 13/04; C12N 9/10; C12N 9/88; C12R 1/19
[52] U.S. Cl. .................. 435/106; 435/193; 435/232; 435/849
[58] Field of Search .................. 435/106

[56] References Cited

U.S. PATENT DOCUMENTS

| | | | |
|---|---|---|---|
| 3,036,958 | 5/1962 | Asai et al. | 435/108 |
| 3,183,170 | 5/1965 | Kitai et al. | 435/116 X |
| 3,458,400 | 7/1969 | Chibata et al. | 435/116 |
| 3,463,704 | 8/1969 | Okumura et al. | 435/116 |
| 3,767,528 | 10/1973 | Nagasaki et al. | 435/108 |
| 3,898,128 | 8/1975 | Chibata et al. | 435/116 X |
| 4,304,858 | 12/1981 | Wandrey et al. | 435/115 |

OTHER PUBLICATIONS

Tosa et al., in Applied Microbiology, vol. 27, pp. 886–889, (1974).
Umbarger et al., in Annual Review of Microbiology, vol. 47, pp. 533–606, (1978).
Herbert, "Oxalacetic Carboxylase of *Micrococcus lysodeikticus*", Methods in Enzymology, vol. 1, pp. 753–757.

*Primary Examiner*—Lionel M. Shapiro
*Attorney, Agent, or Firm*—Sewall P. Bronstein; George W. Neuner

[57] ABSTRACT

A process is described for producing L-4-phenyl-2-amino butanoic acid. The process comprises reacting 4-phenyl-2-oxobutanoic acid or an ester thereof with L-aspartic acid in the presence of transaminase enzyme to produce L-4-phenyl-2-aminobutanoic acid and oxaloacetate, and decarboxylating said oxaloacetate.

12 Claims, No Drawings

PRODUCTION OF L-4-PHENYL-2-AMINOBUTANOIC ACID BY TRANSAMINATION

This application is a continuation-in-part of copending application Ser. No. 528,730 filed Sept. 4, 1983.

This invention relates to the production of L-alpha amino acids (L-amino acids) and derivatives thereof, and in particular, to the production of L-amino acids and their derivatives by transamination between L-aspartic acid and alpha-keto acid compounds corresponding to the desired amino acids, and more particularly to the production of L-4-phenyl-2-aminobutanoic acid.

BACKGROUND OF THE INVENTION

Inhibitors of angiotensin-converting enzyme have been shown to have great potential as anti-hypertensive drugs. A number of clinically promising angiotensin-converting enzyme (ACE) inhibitors contain as a common structural component, the molecule L-4-phenyl-2-aminobutanoic acid. This molecule is an "unnatural" L-amino acid, with a structure analogous to the 20 natural L-amino acids.

Methods currently in use for the production of amino acids include extraction, chemical synthesis followed by resolution, fermentation and enzymatic synthesis (biocatalysis). Extraction procedures require extensive purification of the amino acid of interest from protein hydrolyzates. With chemical synthetic methods, normally a racemic mixture is formed, and the resolution to produce the optically active product is often costly and inefficient. Fermentation, while overcoming many of the disadvantages inherent in the previously mentioned methods, suffers from problems of slow rates of conversion, dilute solutions, costly purifications, and very high capital costs. Biocatalysis offers the potential for lower cost production in many cases primarily because of the significantly reduced capital requirements, lower purification costs due to the absence byproducts in the product stream, and higher rates of conversion of substrates to products because fewer enzymatic steps are involved.

Currently, L-4-phenyl-2-aminobutanoic acid is produced by classical chemical resolutions of the D,L-mixture. The unused D-isomer may be either racemized and recycled or discarded. It would be highly desirable to have a process that produces only the L-isomer directly in essentially quantitative yields in a single reaction step.

SUMMARY OF THE INVENTION

The present invention provides a a method for producing only the L-isomer of 4-phenyl-2-aminobutanoic acid in high yield. In the process of the present invention, L-aspartic acid and 4-phenyl-2-oxobutanoic acid are reacted in the presence of a transaminase to form L-4-phenyl-2-aminobutanoic acid and oxaloacetate, followed by decarboxylation of said oxaloacetate to form pyruvic acid. The decarboxylation of oxaloacetate is essentially irreversible and drives the reaction to completion. Yields of 95% or more of the desired L-amino acid are readily obtained. The by-product, pyruvic acid, is readily separated from the L-amino acid and is highly marketable.

DETAILED DESCRIPTION OF THE INVENTION

In accord with this invention a class of enzymes known as transaminases (aminotransferases) catalyze the general reaction:

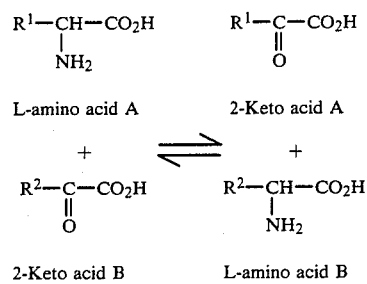

By choosing the proper 2-keto acid precursor B, a desired L-amino acid B can be produced by transamination using another L-amino acid A as the amino donor. As a byproduct of the reaction, a second 2-keto acid A is produced along with the desired L-amino acid B. By selecting 4-phenyl-2-oxobutanoic acid as the 2-keto acid B, L-4-phenyl-2-aminobutanoic acid is made.

The advantages of this transamination technology are:
1. L-amino acids are produced specifically.
2. The 2-keto acid precursors are conveniently available from chemical synthesis.
3. The rates of reaction are relatively rapid.
4. The capital costs are lower than for a fermentation process.
5. The technology is general because transaminases with varying selectivities are available, e.g. aromatic amino acid transaminases, branched chain amino acid transaminases, transaminases specific for amino acids having acidic side chains, etc. Such transaminases can be prepared, for example, from the following microorganisms: *Escherichia coli* (*E. coli*), *Bacillus subtilis*, *Bacillus stearothermophilus Achromobacter eurydice*, *Klebsiella aerogenes*, *Pseudomonas putida*, *Saccharomyces cerevisiae*, and the like. Some transaminases useful in the practice of this invention are also described by H. E. Umbarger in *Annual Rev. Biochem.* Vol. 47, pp. 533–606 (1978). Pyridoxal phosphate is used as a co-factor in the reaction.

One transaminase demonstrated to be useful in the practice of the present invention is the aspartic-glutamic transaminase from *E. coli* K-12. This enzyme catalyzes the transamination of several natural L-amino acids in addition to L-aspartic acid and L-glutamic acid, including L-methionine, L-phenylalanine, L-tyrosine, L-tryptophan, and L-leucine. I have found that this enzyme catalyzes the unnatural reaction of L-glutamic acid (or L-aspartic acid) and 4-phenyl-2-oxobutanoic acid to produce 2-ketoglutarate (or oxaloacetate) and L-4-phenyl-2-aminobutanoic acid at a rate approximately 16–18% of that for the transamination of phenylpyruvic acid to L-phenylalanine.

The single greatest disadvantage of this general method is that the equilibrium constant for the transamination reaction as written above is about 1.0. As a result, the yield of the desired amino acid for the reaction as written will never exceed approximately 50%. This problem is solved by the preferred embodiment of the present invention by using L-aspartic acid as the amino donor (L-amino acid A) and by converting the byproduct (2-keto acid A), i.e. oxaloacetate, by an irreversible reaction, decarboxylation, to pyruvic acid.

Preferably, the irreversible decarboxylation of oxaloacetate is coupled to the transamination reaction. Thus, the transamination reaction is driven to completion, as shown below:

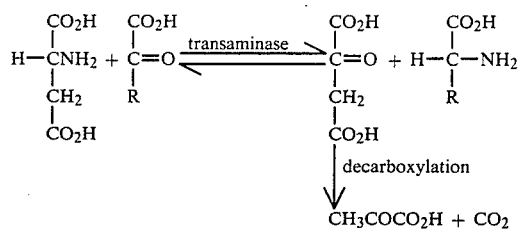

By coupling the decarboxylation of the oxaloacetate to the transamination reaction in accord with this invention, the production of L-amino acids in high yield can be obtained by this biocatalytic method. Using this method, the conversion of the 2-ketoacid precursor B to the desired L-amino acid B in yields approaching 100% have been achieved.

The decarboxylation of oxaloacetate can be catalyzed either thermally; chemically by various metal ions, amines and/or acids; or preferably enzymatically by the enzyme oxaloacetate decarboxylase (OAD) E.C. 4.1.1.3. Oxaloacetate decarboxylase from any source can be used. Examples of sources of oxaloacetate decarboxylase useful in the practice of the present invention are, for instance, *Micrococcus luteus,* renamed from *Micrococcus lysodeikticus* (see *Methods in Enzymology* 1, 753–7 (1955) which is incorporated by reference, *Pseudomonas putida* (see *Biochem. Biophys. Acta* 89, 381–3 (1964) which is hereby incorporated by reference), and *Azotobacter vinelandii* (see *J. Biol. Chem.* 180, 13 (1949) which is hereby incorporated by reference), etc. Also, any other enzyme having an oxaloacetate decarboxylase activity but not usually regarded as an "oxaloacetate decarboxylase" may be used such as, for instance, pyruvate kinase, malic enzyme, etc. The activity of oxaloacetate decarboxylase can be enhanced by adding metal ions such as, for example, $Mn^{++}$, $Cd^{++}$, $Co^{++}$, $Mg^{++}$, $Ni^{++}$, $Zn^{++}$, $Fe^{++}$, $Ca^{++}$ and the like.

The process of this invention can thus be used for the production of L-4-phenyl-2-aminobutanoic acid from 4-phenyl-2-oxobutanoic acid in yields approaching 100% of theoretical.

The byproduct of the decarboxylation of oxaloacetate, pyruvic acid, is a valuable commerical product and can be recovered from the product stream by any method described in the prior art, such as acidification and distillation, ion exchange, solvent extraction, and the like.

The enzymes can be added to the reaction mixture in whole cells, crude cell lysates, as partially purified enzyme or purified enzyme. Preferably partially purified or purified enzymes are used, either immobilized or in solution, because the conversion rates per unit of enzyme are higher. The enzymes can be purified by techniques well known to those skilled in the art. Examples of purification of oxaloacetate decarboxylase from *Micrococcus luteus* and *Pseudomonas putida* are described by Herbert, *Methods in Enzymology* 1, pp. 753–57 (1955) and by Morton et al., *Biochem. Biophys. Acta.* 89, pp. 381–83 (1964).

The enzymes can be used in solution or as immobilized enzymes, as aforesaid, in the practice of this invention. One example of an immobilized enzyme system is described by Weetall et al., *Methods in Enzymology* 34, pp. 59–72 (1974), which is hereby incorporated by reference. Weetall et al. describe a method for immobilizing enzymes on glutaraldehyde activated controlled pore glass beads (Corning).

In accord with this method, transaminase can be coupled to the glass particles by reacting the enzyme with the activated glass particles at 0°–5° C. for 2 hours in a phosphate buffer solution having a pH of 7.0. The coupled enzyme can be used directly or first reacted with 1% sodium borohydride to stabilize the covalent link between the enzyme and the activated glass.

Other suitable substrates for immobilizing enzymes for the practice of this invention include porous ceramic, kiselguhr, diatomaceous earth, sepharose, diethylaminoethyl cellulose, carrageenan, alginate and the like. These substances can be activated, if desired, by techniques well known in the art.

The reaction of L-aspartic acid and 2-keto-4-phenylbutanoic acid to produce L-4-phenyl-2-aminobutanoic acid and pyruvic acid can be monitored if desired. A general assay which is applicable to the assay of all transamination reactions using L-aspartic acid as the amino donor regardless of the 2-keto acid precursor that is used is the following: L-aspartic acid, a 2-keto acid, transaminase, NADH, and the enzyme malic dehydrogenase (available commercially) are dissolved in solution of phosphate buffer as a pH between 6.0 and 9.0; the change in the absorbance at 340 nm ($A_{340}$) with time is measured. This change in the absorbance at 340 nm corresponds to the consumption of NADH during the reduction of oxaloacetate, formed from L-asparate during the transamination reaction.

The invention will now be further illustrated by the following examples which are given here for illustrative purposes only and are not intended to limit the scope of the invention.

EXAMPLE 1

Preparation of Transaminase

*E. coli* K-12 maintained on L-broth plates was innoculated into 2.0 liter shake flasks containing 500 ml of the medium listed below:

| | |
|---|---|
| $KH_2PO_4$ | 5 g/Liter |
| $K_2HPO_4$ | 5.56 g/liter |
| $(NH_4)_2SO_4$ | 2 g/liter |
| $MgSO_4$ | 75 mg/liter |
| $Na_3(citrate).2H_2O$ | 1 g/liter |
| *Trace Metals | 3 ml/liter |
| Glucose | 10 g/liter |

*Preparation of Trace Metals Solution

| Metal Salts | Amount | Final concentrations |
|---|---|---|
| $FeCl_3.6H_2O$ | 27 g/l | 300 $\mu$M |
| $ZnCl_2$ | 1.3 g/l | 30 $\mu$M |
| $CoCl_2.6H_2O$ | 2 g/l | 25 $\mu$M |
| $Na_2MoO_4.2H_2O$ | 2 g/l | 25 $\mu$M |
| $CaCl_2.2H_2O$ | 1 g/l | 20 $\mu$M |
| $CuCl_2.2H_2O$ | 1.27 g/l | 22 $\mu$M |
| $H_3BO_3$ | 0.5 g/l | 24 $\mu$M |
| HCl (conc) | 100/ml/l | 3.6 $\mu$M |

Growth was at 37° C. for 15 hours. These flasks were used to innoculate 14 liter Biolafitte fermenters (1 liters of shake flask culture into 7 liters) containing 7 liters of the growth medium listed below:

| | |
|---|---|
| KH$_2$PO$_4$ | 2.0 g/liter |
| K$_2$HPO$_4$ | 3.6 g/liter |
| (NH$_4$)$_2$SO$_4$ | 750 mg/liter |
| Na$_3$(citrate).2H$_2$O | 1 g/liter |
| Trace metals | 3 ml/liter |
| Pump in glucose as needed. | |

Growth was at 37° C. with aeration at 300 rpm and the pH was maintained at 6.9 by titration with ammonium hydroxide. The cells were harvested by centrifugation at 4000 rpm and frozen at −10° C. until needed.

Purification of the Aromatic Acid Transaminase

All steps were carried out at 4° C. Centrifugations were carried out in a Sorvall RC2B centrifuge.

1. E. coli K-12 cells (80 g wet weight) were resuspended in 200 ml of an aqueous buffer solution, pH 7.0, containing 200 mM potassium phosphate, 1 mM ethylenediaminetetraaccetic acid (EDTA) disodium salt, 1 mM beta-mercaptoethanol, 1 mM pyridoxal phosphate, and 0.02% (weight/volume) sodium azide. The cells were sonicated using a Heat Systems - Ultrasonics Cell Disruptor with 4 one minute bursts, power setting 9. The cell debris was separated by centrifugation at 12,000 rpm for 20 minutes.

2. The crude extract (supernatant from step 1) was made 1.25% weight/volume in streptomycin sulfate by adding the appropriate amount of a 40% streptomycin sulfate solution prepared in the buffer of step 1. The mixture was stirred slowly for 20 minutes then centrifuged at 12,000 rpm for 20 minutes. The precipitate was discarded.

3. The protein in the supernatant from step 2 was fractioned by the addition of ammonium sulfate. Crystalline ammonium sulfate was added with stirring until a concentration 40% of saturation was attained and the protein precipitate was centrifuged and discarded. Additional ammonium sulfate was added with stirring until a concentration 70% of saturation was attained and the protein precipitate was centrifuged, collected, and redissolved in the minimum amount of a buffer, pH 6.5, containing 0.03 M sodium phosphate, 1 mM ethylenediaminetretraacetic acid disodium salt, 1 mM beta-mercaptoethanol, and 0.02% (weight/volume) sodium azide. This solution was dialyzed against 2 liters of the same buffer (18 hours, 2 changes of buffer).

4. A DEAE-cellulose column (Whatman DE-52, 1.6 × 30 cm) was equilibrated with the buffer from step 3. The sample was loaded on the column and washed until no more protein could be detected in the effluent as measured by the OD$_{280}$ (<0.02). A 0–0.5 M NaCl linear gradient was established, 250 ml total volume, flow rate =4 ml/10 minutes/fraction. Transaminase activity eluted between 0.09 and 0.2 M NaCl and was pooled and dialyzed against 2×2 liters of a buffer, pH 6.5, containing 0.03 M sodium phosphate, 1 mM ethylenediaminetetraacetic acid disodium salt, 1 mM beta-mercaptoethanol, 0.02 mM pyridoxal phosphate.

5. The transaminase solution was loaded onto a column of hydroxyapatite (2.6×30 cm) and equilibrated in the dialysis buffer of step 4. The transaminase activity was not retained by the column and was concentrated to approximately 4 ml using an Amicon ultrafiltration apparatus with a YM 30 membrane.

6. The concentrated transaminase from the previous step was loaded onto a Sephacryl S-200 column, 2.6×90 cm, in a solution of 0.05 M Tris pH 8.0, 0.02 mM pyridoxal phosphate, 1 mM ETDA, and 1 mM beta-mercaptoethanol. Elution with the same buffer gave a band of transaminase activity eluting soon after the void volume. This material was stored at 4° C. and was stable for at least 4 months.

Oxaloacetate decarboxylase can be prepared from *Micrococcus luteus, Pseudomonas putida*, or the like, by similar procedures as is well known in the art.

EXAMPLE 2

Preparation of L-4-phenyl-2 amino butanoic acid by E. coli K-12 Transaminase

Ethyl 4-phenyl-2-oxobutanoate (Chemical Dynamics) (206 mg, 1 mMole) was suspended in 10 milliliters of 1.0 M NaOH, and the mixture wa stirred for 30 minutes until the pH dropped to below 8.6, indicating complete hydrolysis of the ethyl ester. The mixture was centrifuged briefly, and the colorless supertanant containing 4-phenyl-2-oxobutanoic acid sodium salt was decanted. A solution containing 0.700 ml pH 8.0 50 mM potassium phosphate buffer, 0.10 ml of the above 4-phenyl-2-oxobutanoate solution, 0.050 ml, 500 mM disodium L-aspartate, 1.0 international until of malic dehydrogenase 0.1 international units of aspartic transaminase purified from E. coli K-12, 0.1 micromole pyridoxal phosphate (Sigma), and 0.25 mg nicotinamide adenine dinucleotide in the reduced form (Sigma). The decrease in the absorbance at 360 nm was indicative of reaction. This change was not observed in controls in which transaminase, malic dehydrogenase, L-aspartate, or 4-phenyl-2-oxobutanoate were the only component omitted. The rate of the reaction was approximately 16–18% of the corresponding reaction using phenylpyruvate in place of 4-phenyl-2-oxobutanoate.

EXAMPLE 3

Production of L-4-Phenyl-2-Aminobutanoic Acid By Immobilized Enzymes

Transaminase from *E. coli* K-12 and oxaloacetate decarboxylase from *Pseudomonas putida* ATCC 950 are immobilized on succinyl aminoproply porous glass (Corning) by covalent attachment using the carbodiimide method described by Weetall. The immobilized enzyme is loaded into a shall column. A solution of 2-keto-4-phenylbutanoic acid (18 g/liter), L-aspartic acid (15 g/liter), pyridoxal phosphate (0.05 g/liter), MgO$_2$. 6H$_2$O (2.03 g/liter) buffered by 50 mM potassium phosphate with a pH of 7.1 is pumped through the column and the effluent is collected in fractions. The extent of conversion is monitored by assaying the pyruvic acid using lactic dehydrogenase. The L-4-phenyl-2-aminobutanoic acid and pyruvic acid products are purified by ion exchange chromatography to yield pure L-4-phenyl-2-aminobutanoic acid ($[\alpha]_D^{20} = -47°$) and pyruvic acid.

The invention has been described in detail including the preferred embodiments thereof. However, it will be appreciated that those skilled in the art, upon consideration of the disclosure herein, may make modifications and improvements within the spirit and scope of the invention.

What is claimed is:

1. A process for producing alpha L-4-phenyl-2-aminobutanoic acid or derivatives thereof, said process comprising reacting 4-phenyl-2-oxobutanoic acid or an ester thereof with L-aspartic acid in the presence of transaminase enzyme to produce L-4-phenyl-2-aminobutanoic acid and oxaloacetate, and decarboxylating said oxaloacetate.

2. The process of claim 1 wherein the said transaminase is a purified or partially purified enzyme preparation, or is contained within a whole cell.

3. The process of claim 1 wherein said transaminase is aspartic glutamic transaminase from *E. coli* K-12.

4. The process of claim 1 wherein the said step of decarboxylating oxaloacetate is accomplished using an oxaloacetate decarboxylase enzyme.

5. The process of claim 4 where the said oxaloacetate decarboxylase enzyme is a purified or partially purified enzyme preparation, or is contained within a whole cell.

6. The process of claim 4 wherein said transaminase and said oxaloacetate decarboxylase are each immobilized on an insoluble support.

7. The process of claim 6 wherein said immobilization support is controlled pore ceramic particle or controlled pore glass particle.

8. The process of claim 6 wherein said transaminase and said oxaloacetate decarboxylase ar both immobilized on the same support.

9. The process of claim 6 wherein the said transaminase and oxaloacetate decarboxylase are adsorbed on diethylaminoethyl cellulose.

10. The process of claim 1 wherein the said transaminase is an enzyme isolated from a microorganism selected from the group consisting of *Escherichia coli, Bacillus subtilis, Bacillus stearothermophilus Saccharomyes cerevisiae, Pseudomonas putida, Achromobacter eurydice,* or *klebsiella aerogenes*.

11. The process of claim 4 wherein the said oxaloacetate decarboxylase is an enzyme isolated from a microorganism selected from the group consisting of *Micrococcus luteus, Pseudomonas putida,* or *Azotobacter Vinelandii*.

12. The process of claim 4 wherein the said oxaloacetate decarboxylase is reacted in the presence of a metal ion selected from the group consisting of $Mn^{++}$, $Cd^{++}$, $Co^{++}$, $Mg^{++}$, $Ni^{++}$, $Zn^{++}$, $Fe^{++}$, and $Ca^{++}$.

* * * * *